(12) United States Patent
Kasten

(10) Patent No.: US 6,440,143 B2
(45) Date of Patent: Aug. 27, 2002

(54) HAND-HELD DEVICE FOR PREPARATION OF A SKIN GRAFT BY TANGENTIAL EXCISION OF LAYERS OF TISSUE

(76) Inventor: Klaus Kasten, Kopernikusallee 9, 75175 Pforzheim (DE)

( * ) Notice: Subject to any disclaimer, the term of this patent is extended or adjusted under 35 U.S.C. 154(b) by 0 days.

(21) Appl. No.: 09/729,925

(22) Filed: Apr. 24, 2001

(30) Foreign Application Priority Data

Dec. 7, 1999 (DE) .......................................... 199 58 855

(51) Int. Cl.$^7$ .............................................. A61B 17/00
(52) U.S. Cl. ........................ 606/132; 606/131; 30/375
(58) Field of Search ................................ 606/132, 131, 606/82; 30/43.7, 373–375, 182, 185

(56) References Cited

U.S. PATENT DOCUMENTS

| | | | | |
|---|---|---|---|---|
| 2,582,511 A | * | 1/1952 | Stryker | 606/132 |
| 3,364,920 A | * | 1/1968 | Ross | 606/132 |
| 4,038,986 A | * | 8/1977 | Mahler | 606/132 |
| 4,098,278 A | * | 7/1978 | Schwartz | 606/132 |
| 4,665,915 A | * | 5/1987 | Grollimund | 606/132 |
| 4,690,139 A | * | 9/1987 | Rosenberg | 606/132 |
| 4,917,086 A | * | 4/1990 | Feltovich et al. | 606/132 |
| 5,004,468 A | * | 4/1991 | Atkinson | 606/132 |
| 5,209,755 A | * | 5/1993 | Abrahan et al. | 606/132 |
| 5,219,352 A | * | 6/1993 | Atkinson | 606/132 |
| 5,306,279 A | * | 4/1994 | Atkinson | 606/132 |
| 5,873,881 A | * | 2/1999 | McEwen et al. | 606/132 |
| 6,063,094 A | * | 5/2000 | Rosenberg | 606/132 |

* cited by examiner

*Primary Examiner*—Jeffrey A. Smith
*Assistant Examiner*—Michael B. Priddy
(74) *Attorney, Agent, or Firm*—Browdy and Neimark, P.L.L.C.

(57) ABSTRACT

Hand-held appliance for preparation of an excised skin graft, that is placed upon a plane surface, by tangential excision of tissue below the epidermis to produce a trimmed skin graft of desired remaining tissue layers and thickness with a blade that is held between two holding rods, that can be placed on a plane surface and that is held in a height-adjustable axis parallel to the surface. The end regions of the rods are shaped so that the distance between the axis and the contact surface of the edge of the end regions to the surface changes at least by sections, while the minimal distance and the maximal distance define the lowest and the highest cutting plane, respectively, so that the distance of the cutting plane is defined by the operating angle between the plane of the rods and the surface.

11 Claims, 2 Drawing Sheets

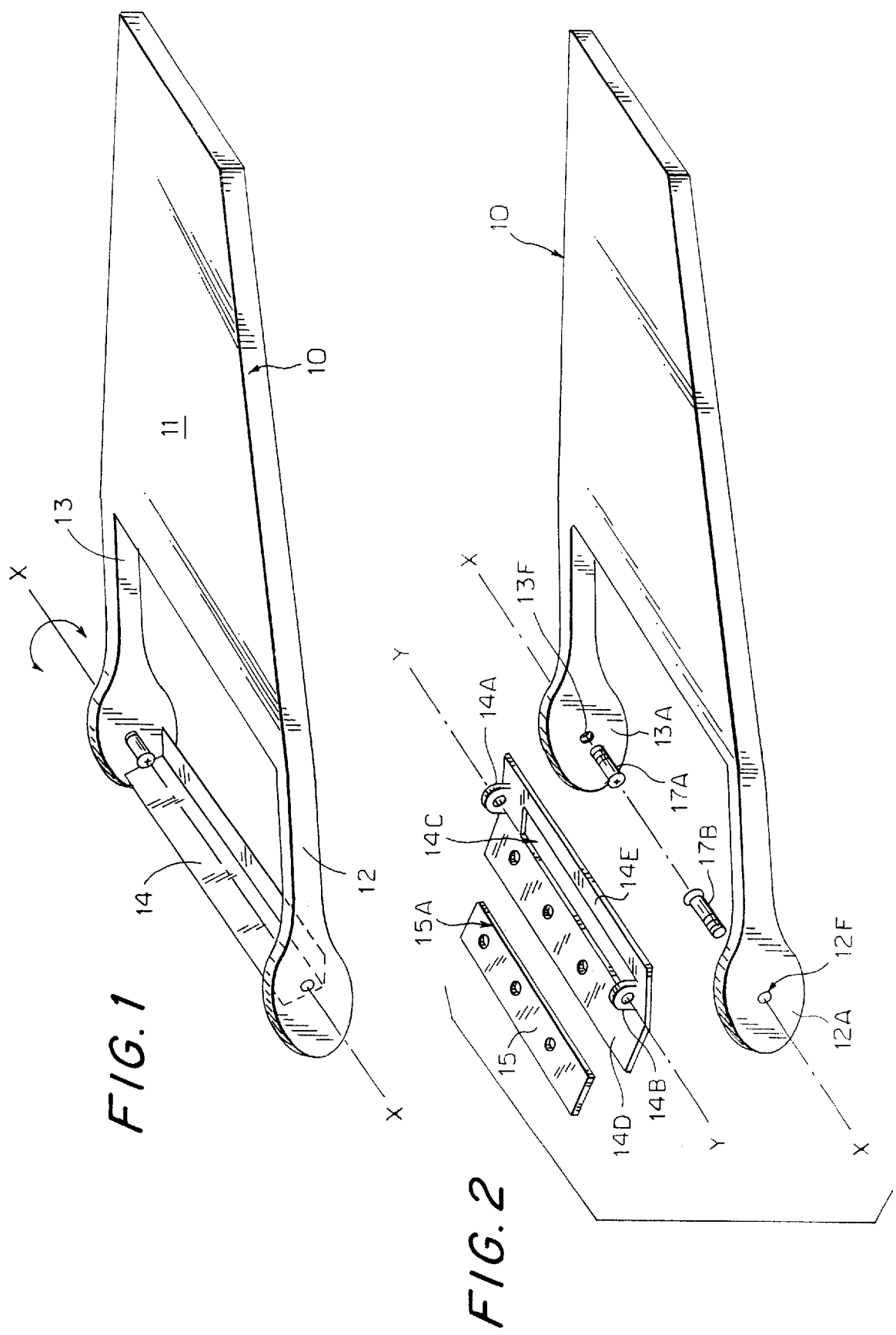

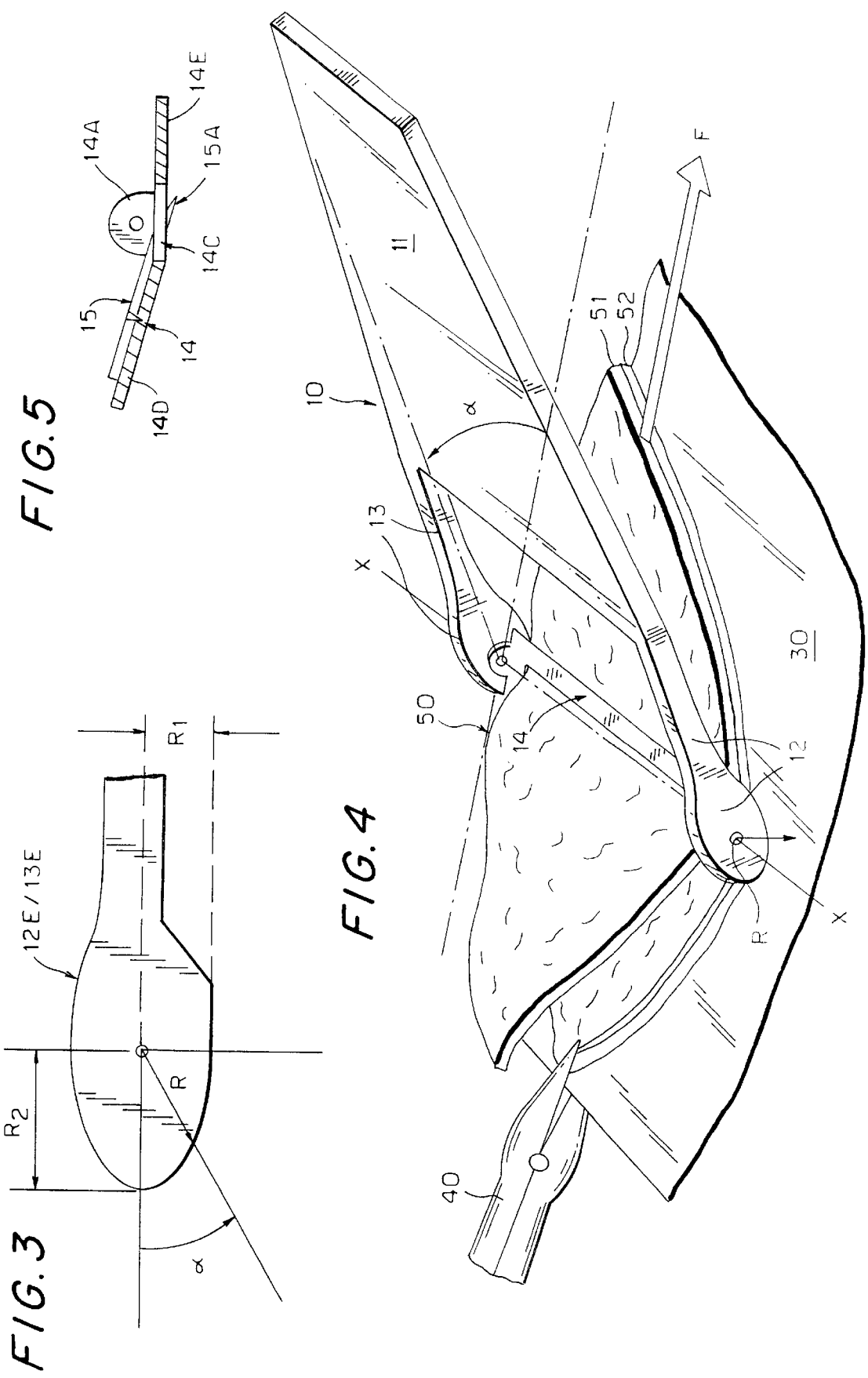

HAND-HELD DEVICE FOR PREPARATION OF A SKIN GRAFT BY TANGENTIAL EXCISION OF LAYERS OF TISSUE

TECHNICAL BACKGROUND OF THE INVENTION

The invention refers to a hand-held device according to the preamble of the patent claim 1.

Skin grafting for surgical or cosmetic purposes constitutes an essential part of surgical maneuvers, especially for broad wounds resulting from injury or from removal of a skin tumor. According to the medical indication and the recipient site, e. g. in the facial region for cosmetic purposes, skin grafts of divergent thickness, which comprise all or only some tissue layers of the skin are used. Thus, one differentiates e. g. full-thickness skin grafts (FTSG), which comprise epidermis and complete dermis from split-thickness skin grafts (STSG), which include epidermis and only a part of the dermis.

There are various procedures for graft taking, that are not of detailed concern in consideration of the invention under discussion, like the excision of the desired skin layer for grafting by mechanical or electromechanical devices (so-called dermatomes), besides the manual excision of the skin graft of desired size using a blade, knife or scalpel.

The above mentioned context and medical requirements are described in detail in the publication "Journal of the American Academy of Dermatology", Vol. 27, No. 2, part 1 (August 1992). Different realizations of dermatomes are known in medical engineering, represented e. g. by the patent claims U.S. Pat. No. 4,690,139 and GB 774 689.

PRIOR ART

Generally, it is not possible to place the excised "raw" graft directly on the recipient site in a medically suitable way, as thickness and type of tissue layers of the skin graft require further manipulation, respectively preparation, to remove undesired tissue layers, e. g. subcutaneous fat and to adapt the underside of the skin graft to the recipient site optimally.

In the first-mentioned publication (page 155, last paragraph) a manual procedure of preparing a skin graft is described shortly: The skin graft is draped raw side up (epidermal side down) over a finger or another region of the hand of the surgeon and the undesired subcutaneous fat or subcutaneous fat and dermal tissue is trimmed with scissors until the desired skin thickness is obtained. Obviously, this conventional method to trim a skin graft is not optimal, as it depends solely on the manual skills of the surgeon and an even thickness of the whole graft is not warranted. There is also a risk of contamination for the skin graft resulting from the tight contact to the hand of the surgeon, who is at risk of injuring himself while using scissors just above the surface of his hand. Finally, a perforation of the skin graft cannot be excluded.

This basically manual and time-consuming method hence does not provide optimal requirements for successful grafting in a hygienic respect, as well.

For these reasons, different more or less complicated devices have been published to accomplish this procedure more reliably (DE 297 22 914 U1; DE 94 03 937 U1); a kind-like device is known from U.S. Pat. No. 3,364,920. A slicer-like apparatus is shown there, wherein a blade for removal of undesired tissue layers is adjustable in a certain position, wherein a given distance of the cutting level to a surface, where the skin graft is placed upon, and by this the remaining thickness of the skin graft, is maintained whilst cutting as the lateral rods of this device move along both sides of the skin graft on the surface.

Even though this device offers more reliability than the beforehand described manual preparation with scissors, it is cumbersome and the adjustment of the blade position is laborious, which is especially disadvantageous, if the once adjusted distance between the blade and the surface does not directly result in the desired remaining thickness of the skin graft. The multitude of components requires a high precision in its production and makes this known device uneconomical.

PRESENTATION OF THE INVENTION

The task of the invention hence is to simplify the known hand-held device regarding its handling and construction with keeping a desired thickness of a skin graft.

This task is solved with the features of the patent claim 1.

The basic idea of the invention consists in keeping a definite cutting plane along the whole cutting movement solely by the handling of the device while drawing it through the graft, but also to allow corrections of the cutting plane while pulling through the blade. To realize this advantage the invented contraption is intended to be provided with two rods, with their end regions serving as variable spacers, so that according to the applicable operating angle of the device in relation to the supporting surface a definite thickness of the remaining skin tissue can be chosen quickly and easily. A removal of tissue in multiple layers is also possible with a reduction of the operating angle resulting in a lowering of the cutting plane allowing a quick and nonetheless precise "cautious" approach to the layer of the skin graft later representing the contact surface to the recipient site.

The invented device is handy, easy to use and facile to produce. The time required to trim a graft using this device, is considerably diminished, the danger of injuries and contamination is reduced.

Preferred features are represented in the subsections of the patent claim.

BRIEF DESCRIPTION OF THE DRAWINGS

A preferred example of realization is illustrated with drawings. It is depicted in:

FIG. 1 a perspective illustration of the invented device

FIG. 2 an explosion illustration of the separate components of the device according to FIG. 1

FIG. 3 a detailed illustration of the shape of the end regions of the spacer rods FIG. 4 a perspective illustration of the device in its intended use to elucidate the presented procedure FIG. 5 a sectional view of the cutting element with inserted blade

DESCRIPTION OF PREFERRED EMBODIMENTS

The invented contraption consists of a handheld device 10, with a grip 11 extending into two rods 12,13, the latter having a cutting element rotatorily suspended on an axis X—X between them (FIG. 1).

The cutting element is formed by an angled plate 14 (angled to the longitudinal axis Y—Y) with a longitudinal slit-like aperture 14C, that separates the cutting element spatially and functionally into a blade support 14D and a tautening part 14E, the latter having full contact to the skin graft. The blade 15 is positioned on its support 14D, so that its edge 15A protrudes through the slit-like aperture 14C of the cutting element to the underside and sticks out of the plane of the tautening part 14E, which enables it to cut. The angled axis Y—Y parallels the edge of the slit-like aperture 14C of the blade support 14D (FIG. 5).

On the narrow sides of the slit-like aperture 14C of the plate 14 two slots 14A, 14B are attached, that are supporting the cutting element with the blade 15 with pegs 17A, 17B in bore-holes in the spacer rods 12,13 in an axis of rotation. By this arrangement, the cutting element can move seesaw-like in direction of the double-arrows of FIG. 1 and hence keep up a cutting level parallel to the surface 30, if the hand-held device 10 is moved in a different angle α to the surface 30. This will be further illustrated later.

The end regions 12A, 13A of the spacer rods 12, 13 are formed at their frontal ends so that (FIG. 3) the distance R between the axis of rotation X—X and the lower edge of the end regions 12A, 13A that represent the contact surface of the handpiece 10 to the supporting surface 30 decreases continuously in direction to the grip 11. This means that there is a minimal distance R1 (in the illustrated example perpendicular to the plane of the handpiece 10) and a maximal distance R2 (in the illustrated example in the plane of the handpiece 10), so that the distance R is a function of the angle α.

The handling of the invented device of preparation of an excised skin graft is depicted in FIG. 4:

The excised skin graft 50 is placed with its upper side (epidermis 52) on a plane surface 30 and is fixed with a clamp 40. Then, the device 10 is placed over one side of the skin graft 50 and the blade 15 is drawn through the skin graft, with the edge 15A of the blade 15 cutting layers (subcutaneous fat and dermis) off the tissue 51 of the skin graft 50. With this, the end regions 12A, 13A of the spacer rods 12, 13 have contact with the plane surface 30, so that the distance R defines the distance of the axis of rotation X—X and hence the cutting edge 15A to the surface. As this distance R depends on the angle α (FIG. 3), and likewise the inclination of the device 10 towards the surface 30 is defined by this angle α as an operating angle between the surface 30 and the plane of the handpiece (alternate angles), the cutting depth of the blade 15 over the surface 30 and hence the thickness of the remaining tissue can be reliably chosen and maintained by the surgeon by the operating angle α.

The tautening part 14E of the cutting element slides over the surface of the respectively last remaining tissue layer to secure an even cutting level resulting in a smooth and neat cut by the edge of the blade 15A. The thickness of tissue, that is cut off in one cutting process is also dependent on the difference in height between the cutting edge 15A and the tautening part 14E, with the latter spreading and tautening the skin graft before the cutting by the cutting edge 15A takes place.

This procedure can be repeated until the cutting depth according to the distance R corresponds to the wanted thickness of the skin graft, which can then be taken off of the surface 30 and used for its purpose.

The cutting plane of the blade 15A has to be lowered in the following cutting processes as the thickness of the remaining skin graft decreases, which can be accomplished by reducing the operating angle α respectively by a flatter position of the device 10. Hereby it becomes evident, that the end regions 12A, 13A operate as spacers for the edge of the blade 15A in regard to the surface 30 and that their shape enables the surgeon to choose an infinitely variable cutting depth by selecting the adequate operating angle α.

In a preferred example the shape of the end regions 12A, 13A is selected so that the minimal distance R1 is reached at an operating angle α of 35°, with R1 and R2 being selected as 0.75 mm and 5 mm, respectively.

The described procedure using the invented device hence advantageously enables the removal of unwanted tissue of a skin graft precisely and evenly in one or more cutting processes resulting in a skin graft of precisely adjustable and totally even thickness.

While the invention has been described with respect to a number of preferred embodiments, it will be appreciated that these are shown for purposes of example, and that many other variations, modifications, and applications of the invention may be applied, e. g. the integration in an apparatus for automatic guidance of the device.

What is claimed is:

1. A hand-held appliance for preparation of an excised skin graft that is placed upon a surface, by tangential excision of tissue below the epidermis to produce a trimmed skin graft of desired remaining tissue layers and thickness, said appliance comprising: a grip element provided with two holding rods lie in a plane and that can be placed on the surface when said appliance is in use; and a blade mounted between said holding rods in a manner to be pivotally movable relative to said holding rods about an axis, wherein: said grip element is orientable to place said plane at a selected angle relative to the surface; each of said holding rods has an end region delimited by an edge that bears on the surface when said appliance is in use and that is shaped so that different points along said edge are at different distances from the axis such that a variation in the selected angle when said edges bear against the surface causes a corresponding variation in the distance between said blade and the surface for cutting the excised skin graft to a selected thickness.

2. The hand-held appliance according to claim 1, wherein each of said end regions is shaped approximately like a semi-ellipse.

3. The hand-held appliance according to claim 1, wherein the distances between each said edge and the axis is between 0.75 mm and 5 mm.

4. The hand-held appliance according to claim 1, further comprising a tautening and spreading unit installed parallel to and functionally before said blade between said holding rods to taunten and spread the skin graft.

5. The hand-held appliance according to claim 4, wherein said blade and said tautening and spreading unit are adjusted in such a manner that the deepest cutting level is reached at an operating angle of about 20°–30° between said plane and the surface.

6. The hand-held appliance according to claim 4, wherein said blade and said tautening and spreading unit are parts of one combined pivotable cutting element.

7. The hand-held appliance according to claim 6, wherein said blade and said tautening and spreading unit are adjusted in such a manner that the deepest cutting level is reached at an operating angle of about 20°–30° between said plane and the surface.

8. The hand-held appliance according to claim 6, wherein the cutting element is an angled plate that is angled in a longitudinal axis with a slit-like aperture in a middle region of said plate, said aperture dividing the cutting element into a support for said blade and said tautening and spreading unit.

9. The hand-held appliance according to claim 8, wherein: said plate has two passages at opposite ends of said aperture;

each of said end regions has a bore-hole; and said appliance further comprises two pegs each extending through a respective passage and a respective bore-hole for pivotally mounting said cutting element to said grip element.

10. The hand-held appliance according to claim 8, wherein said blade has a cutting edge and is positioned on said support so that said cutting edge protrudes through said slit-like aperture to an underside of said plate and protrudes past said underside.

11. The hand-held appliance according to claim 1, wherein said blade is held between said end regions.

\* \* \* \* \*